United States Patent [19]

Korpman

[11] 4,449,977
[45] May 22, 1984

[54] ABSORBENT PRODUCTS, PROCESSES AND COMPOSITIONS

[75] Inventor: Ralf Korpman, Bridgewater, N.J.

[73] Assignee: Johnson & Johnson, New Brunswick, N.J.

[21] Appl. No.: 329,642

[22] Filed: Dec. 11, 1981

Related U.S. Application Data

[63] Continuation-in-part of Ser. No. 088,882, Oct. 29, 1979, abandoned.

[51] Int. Cl.³ .............................................. A61F 13/16
[52] U.S. Cl. ..................................... 604/366; 604/370
[58] Field of Search ............... 604/327, 329, 330, 331, 604/358, 328, 366, 346–354, 370; 521/65, 84, 905, 916; 260/17 R, 17.4 BB, 17.4 ST, 17.4 UC

[56] References Cited

U.S. PATENT DOCUMENTS

4,197,371  4/1980  Holst et al. ........................... 521/84

Primary Examiner—C. Fred Rosenbaum
Assistant Examiner—T. J. Wallen
Attorney, Agent, or Firm—Alice O. Robertson; Leonard Kean

[57] ABSTRACT

A flexible non-disintegrative absorbent product comprising a water-insoluble substantially non-swelling matrix of a thermoplastic polymer bearing a uniformly dispersed particulate water-insoluble water-swellable organic polymer absorbent. Certain compositions and processes for their preparation as well as article prepared from the products are described.

9 Claims, 8 Drawing Figures

ABSORBENT PRODUCTS, PROCESSES AND COMPOSITIONS

This application is a continuation-in-part application of applicant's copending application, Ser. No. 088,882, filed Oct. 29, 1979, now abandoned.

The present invention relates in general to nondisintegrative aqueous-fluid-absorbent products, processes and compositions.

BACKGROUND OF THE INVENTION

Retention and or removal of water or aqueous liquids, particularly body fluids, are frequently accomplished by use of absorbent bearing materials and articles manufactured therefrom. Representative articles include diapers, incontinence pads, sanitary napkins, bibs, wound dressings and the like. Generally, absorption is achieved by use of cellulosic and modified cellulose materials. Where the intended use contemplates absorption of relatively large volumes of liquids such as diapers, sanitary napkins and the like, the cellulosic materials are in the form of fluff or batting. For these uses especially, there are teachings in the literature for distributing particulate materials, sometimes referred to in the art as superabsorbents, throughout the batting or in certain areas thereof. The settling and bunching of the powder or particulate matter encountered during shipping and storage have rendered these modifications of little value in actual practice. Also found in the art are teachings for modifying fibers in the batting to greatly increase their absorbency. These modifications have not avoided the need for a batting which are inherently bulky. Free films of absorbent polymers have been described but they are generally stiff, non-flexible and frequently frangible. Some films have been reported which are flexible but methods for the production of these films employ aqueous medium either during or prior to coating with subsequent removal of water and do not constitute convenient or practical manufacturing operations where time-consuming drying operations necessary for removal of water are sought to be avoided. Absorbents have been distributed in latex but these films are also subject to similar manufacturing drawbacks. Very thin films of absorbent have been coated onto cellulosic fibrous backings which while operable when contained such as in a diaper with topsheet and backsheet are subject to disintegration when not contained. Additionally, absorbents have been incorporated in a foam matrix which may be useful for some applications but are not applicable for thin films or filaments. Although some suggestion has been made of water-insoluble polymeric sheet material broadly as support for absorbent, no actual product is reported or known to be available.

SUMMARY OF THE INVENTION

According to the present invention, there has been devised an aqueous-fluid-absorbent non-disintegrative product which comprises a water-insoluble substantially nonswelling matrix of a thermoplastic polymer having at least partially imbedded therein, particulate water-insoluble but water-swellable organic polymer absorbent. By "water" as herein employed is meant aqueous fluids or liquids and is intended to include such fluids as saline, serum, blood, mucous as well as other aqueous solutions or dispersions. The matrix, of thermoplastic polymer as subsequently defined and non-fibrous, non-textile in nature is insoluble and substantially non-swellable in aqueous systems and resistant to disintegration when wet. The absorbent is selected from organic polymers which are insoluble in water but which are swellable and which absorb many times their own weight of water or aqueous fluid. The organic polymer absorbents may be completely synthetic or may be selected from modified natural molecules, especially modified polysaccharide as hereinafter more fully described.

The product is flexible, is resistant to disintegration when wet, is manufactured in the absence of water, can be made very thin while still being highly absorbent, can be self-supporting or be a coating, can be made in many forms and/or shapes. The forms include film, monofilament, sheet, rope, tubing, etc. and as coating on a substrate, i.e., a supported film.

The product may be prepared by the several procedures which are used in the manufacture of films, filaments and the like. The matrix polymer and the polymer absorbent comprise novel compositions suitable in certain of the methods of preparation and these compositions as well as the use of these compositions in preparing the products constitute an aspect of the present invention.

The absorbent product has numerous applications and is adaptable for use in protective coverings, sanitary napkins, wound dressings, diapers, bed pads, incontinence pads, packaging materials, agricultural blankets and the like. Certain articles which may be prepared employing the novel absorbent bearing polymer products also constitute an aspect of the present invention.

DESCRIPTION OF THE PREFERRED EMBODIMENTS

The absorbent product of the present invention has particulate water-insoluble but water-swellable organic polymer absorbent dispersed on the surface or throughout a water-insoluble substantially non-swelling non-fibrous matrix. Whether dispersed on the surface or throughout the matrix, the particles are dispersed in a manner such that they are at least partially imbedded and are inseparable from the matrix. By "partially imbedded" is meant that most of the particles of the organic polymer absorbent have a portion of the particle surface exposed or protruding above at least one surface of the matrix. Although some individual particles may be completely imbedded, they are generally in a contiguous relationship to particles which are exposed to a surface. In one embodiment of the present invention the particles are dispersed throughout the matrix so that the particles are distributed within the matrix and are exposed to all surfaces of the matrix; in another embodiment, the particles are distributed on one surface of the matrix.

Figures 1, 2, 3, 4, 5:
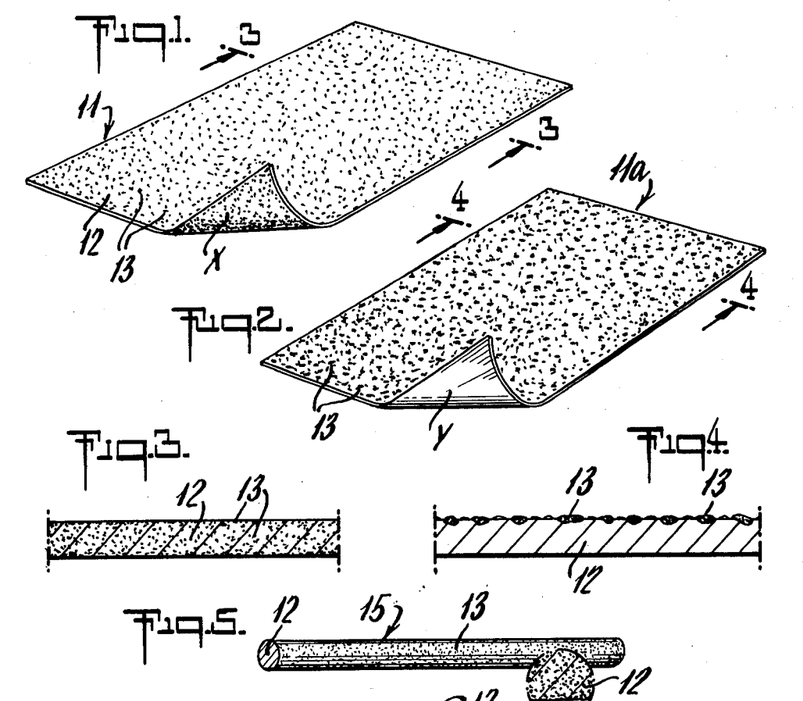
FIG. 1 is a perspective view of an absorbent product in the form of a film and having absorbent dispersed throughout.
FIG. 2 is a partial perspective view of an absorbent product in the form of a film with absorbent on one surface of the film.
FIG. 3 is a partial sectional elevation taken along 3—3 in FIG. 1.
FIG. 4 is a partial sectional elevation taken along 4—4 in FIG. 2.
FIG. 5 is a partial sectional view showing an embodiment of the invention when the absorbent product is in the form of a monofilament.
Figure 6:
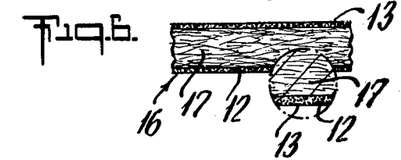
FIG. 6 is a partial sectional view showing an elongated core coated with the absorbent product.

The foregoing may be better understood by reference to the drawings. FIGS. 1 and 3 show a product in the form of a film 11 in which the absorbent particles 13 are dispersed throughout the matrix 12. It can be seen from the area "X" in FIG. 1, representing the underside of the film, that there is absorbent exposed on the underside as well as on the top surface. FIGS. 2 and 4 show a product in the form of a film 11a in which the absorbent 13 is on one surface of matrix 12. The area "Y" in FIG. 2 shows no absorbent exposed on the underside surface. FIG. 5 illustrates absorbent dispersed throughout the matrix when the product is a monofilament 15. FIG. 6 illustrates a coated article 16 with absorbent 13 in matrix 12 in the form of a coating on a core or elongated substrate 17.

The particulate absorbent materials are generally nonfibrous substances in the form of fine, discrete particles which cannot be formed into a fabric web. The particles can have various shapes such as spherical, rounded, angular, acicular, irregular, fragmented and the like. They range in size from about 1 micron to as much as $2 \times 10^4$ microns in diameter or cross-section (largest dimension when not spherical), and are selected from those materials which are generally considered powders and those which are non-pulverous particulate matter. The expression, "powder" is employed to designate particles which are particle size of from about 1 to about $10^3$ microns. When the particulate materials are dispersed throughout and imbedded in the matrix, they are preferably in the form of a powder. When employed in the form of powder and dispersed throughout, the presence of the particles is not always readily apparent; the film or filament oftentimes appears as a smooth film of the matrix polymer. In the embodiment in which the absorbent is borne on one surface of the film, the particles are preferably non-pulverous. The approximate shape and geometry of the particles are retained when the material swells to provide for the binding of the fluid therein.

The matrix is of a thermoplastic polymer and preferably assumes a shape achievable by extrusion. Thus, it may be in the form of a film, sheet, filament, wire rope, tube and the like. Since one of the advantages of the present invention is the rendering available of a very thin and highly flexible material of high absorption capacity, the preferred embodiments of the present invention contemplate use of thin film or fine monofilament as matrix. The matrix may have a thickness ranging from about 1 mil to about 60 mils. The thickness of the film is contemplated generally to be less than about 10 mils. Usually, it will be more than 1 mil preferably in the range of about 2.5 to 5 mils. When the product is in the form of a filament or monofilament, the cross-sectional dimension may be from about 5 to about 60 mils. The expression "filament" or "monofilament" as herein employed is also meant a wire or rope without regard to the cross-sectional dimensions. It is meant to connote a single strand which is not twisted or braided. When the product is in the form a coating on a substrate, the dimensions may be similar to those of unsupported film but generally will be thinner.

The product has a capacity to absorb water or aqueous fluid in an amount of at least 5 times, preferably from about 15 to 40 times or more of the weight of the absorbent in the product. Since the absorptive capacity of the product is dependent on the amount of absorbent in the product, the absorptive capacity of the product depends on the density or on the weight of the absorbent incorporated into a given volume of the matrix. The particulate absorbent material is used in the product in the range of from about 5 to 200 parts, preferably from about 50 to 100 parts for every 100 parts by weight of the matrix polymer. The product efficiently absorbs water and aqueous fluids while retaining flexibility and is resistant to loss of water when subject to pressure.

The particulate absorbent materials to be dispersed in the matrix are organic polymers which may be synthetic organic polymers or which may be modified polysaccharides. In these polymers, hydrophilic groups constitute at least 25 percent and up to about 72 percent of their molecular structure, and the polymeric network is lightly crosslinked introducing a limited water-insolubility into the molecule. Suitable water-insoluble materials have a minimum average molecular weight per cross-linkage of about 13,000 and a maximum molecular weight per cross-linkage of about 276,000. These materials are frequently spoken of in the art as "hydrogels" or "hydrocolloid polymers," and further as "superabsorbents." The preferred polymers have an acrylate group in their molecular structure. They may be completely synthetic acrylate polymers or acrylate modified polysaccharides, e.g., acrylate modified starch or acrylate modified cellulose. "Acrylate" polymers or "polyacrylates" as herein employed embrace not only acrylate salts but also those in which a portion of the hydrophilic group is acrylamide, acrylic acid or acrylate ester. Alternatively, the hydrophilicity may be supplied by a different type of hydrophilic group such as sulfonate, oxide, etc., or by a different type of polymer as hereinafter detailed. Carboxymethylcellulose after cross-linking is also within a scope of suitable absorbents. The absorbent is typically a cross-linked natural or synthetic polymer which without the cross-linking would be water-soluble but which has been lightly cross-linked in ways known in polymer syntheses. The preferred absorbents are cross-linked polymers belonging to one of the following: completely synthetic acrylate polymer, acrylate modified starch, acrylate modified cellulose, and cross-linked carboxymethylcellulose.

Considering first the preparation of the completely synthetic absorbents, it is immaterial in the present invention whether the polymers here to be employed be prepared by supplying appropriate monomer or monomers and thereafter polymerizing, or by polymerizing and thereafter modifying a part of the resulting polymer with recurring moieties. Thus, the polymers may be prepared by cross-linking a preformed water-soluble straight chain polymer, by polymerizing an appropriate monomer or monomer and comonomer and effecting both polymerization and cross-linking, or by incorporating an appropriate group in the polymer structure after completion of the polymerization. An example of the latter is sulfonation after polymerization to obtain polymers bearing sulfonic moieties. Moreover, where it is desired to have the salt form of the carboxylic or sulfonic group, the polymer may be first prepared as an acid, ester, amide or nitrile and the product hydrolyzed in whole or in part.

The preferred of the completely synthetic absorbents are the acrylate type absorbent which includes not only the acrylate salts and acids but also those which have been represented in the literature, e.g., U.S. Pat. No. 3,686,024, by the following formula:

where A is an alkali metal ion such as sodium or potassium, or hydrogen, n is 0.5 to about 0.9, 1-n defines the extent of hydrolysis, and z is the number of mer units between cross-links.

The latter type of acrylate absorbent may be prepared by polymerizing an about 2 to 20 weight percent aqueous solution of acrylamide with from about 0.005 to 0.5 mole percent (based on acrylamide) of a difunctional organic cross-linker such as N,N'-methylenebisacrylamide soluble in the aqueous monomer system in the presence of free radical catalysts to obtain a water-swellable cross-linked polyacrylamide, and thereafter partially hydrolyzing in aqueous alkali to obtain a cross-linked polymer having both carboxamide and alkali metal carboxylate groups as more fully described in U.S. Pat. No. 3,247,171. Alternatively, a linear polyacrylamide may be cross-linked with a cross-linking compound such as N,N'-methylenebisacrylamide, 1,4-divinylbenzene, diallylamine, N,N-diallylmethacrylamide and the like and thereafter hydrolyzing. A polymer having both carboxamide and carboxylate group also may be made by copolymerizing acrylamide and acrylic acid alkali metal salt in the present of cross-linking monomer such as N,N-methylenebisacrylamide in the presence of catalyst system such as equal parts of ammonium persulfate and β-dimethylaminopropionitrile, also described in the aforesaid patent. The former type may be prepared by subjecting a mixture of a monovalent cation salt of acrylic acid in water to the influence of high energy ionizing radiation cross-linking as more particularly described in U.S. Pat. No. 3,229,769, or subject it to chemical cross-linking as described in British Pat. No. 719,330. A number of suitable acrylate absorbents are available commercially, such as PERMASORB (National Starch and Chemical), SAN-WET (Sanyo), "5388" designation (Goodrich), AQUA-KEEP (Mitsubishi), and also are available from The Dow Chemical Company.

Another type of completely synthetic absorbent is a cross-linked poly(alkylene oxide) of molecular weight of at least 100,000 which may be prepared by contacting poly(alkylene oxide) with a suitable cross-linking agent in the presence of a free radical catalyst in a liquid medium containing solvent-nonsolvent mixture for poly(alkylene oxide) wherein the nonsolvent portion constitutes at least 35 percent by weight of the liquid medium, at a temperature sufficiently high to effect cross-linking as more fully described in U.S. Pat. No. 3,956,224. Alternatively, poly(alkylene oxide) may be cross-linked by ionizing radiation as described in U.S. Pat. No. 3,264,202, or co-cross-linked with at least one other water-soluble polymer by exposing aqueous systems of the polymers to high energy radiation to produce cross-linked water-insoluble absorbent polymers as more fully described in U.S. Pat. Nos. 3,957,605 and 3,898,143.

Still another type of completely synthetic polymer absorbent is cross-linked polystyrene sulfonates prepared by known procedures, e.g., by copolymerizing styrene with a non-conjugated divinyl compound such as divinylbenzene in the presence of a polymerization catalyst such as benzoyl peroxide, preferably in the presence of a suspension stabilizer such as gelatin or polyvinyl alcohol, to produce a polymer which is then sulfonated by heating in the presence of concentrated sulfuric acid at a temperature of about 100° C.

Other suitable completely synthetic polymer absorbents include the poly(N-vinylpyrrolidone) type described in U.S. Pat. No. 3,669,103, polyurethane hydrogels described in U.S. Pat. Nos. 3,939,105 and 3,939,123. Still other suitable absorbents are represented by those named in U.S. Pat. Nos. 3,669,103, 3,966,679 and 4,102,340.

Another type of particulate absorbent material suitable for the present purposes is of polysaccharides modified by having grafted thereon hydrophilic chains. By "hydrophilic chains" is meant a polymer chain obtained from monomers which have a water-soluble group or which become water-soluble on hydrolysis, e.g., carboxyl, sulfonic, hydroxyl, amide, amino, quaternary ammonium and hydrolysis products. Representatives of such modified polysaccharides are described in U.S. Pat. No. 4,076,663. Preferred polysaccharides have hydrophilic chains containing a carboxylate group alone or together with a carboxylic or carbamide group attached to starch or cellulose backbone. The modified polysaccharides are sometimes referred to in the literature as starch or cellulose graft copolymers; the preferred graft copolymers hereinafter will be referred to as polysaccharide acrylates, or starch or cellulose acrylates. In these polysaccharide acrylates, the hydrophilic chain is attached to the backbone of the cellulose or starch molecule through a carbon linkage. Thus, a modified cellulose may be represented by the formula wherein L represents a hydrophilic chain of the general formula wherein represent acid, ester, alkali metal or ammonium salt, or amide groups, each R independently is hydrogen or lower alkyl, r is an integer of 0 to about 5000 and s is an integer of from 0 to about 5000, and r plus s is at least 500. A starch graft copolymer, would be similar but would have a starch backbone. These polysaccharide acrylates may be prepared, for example, by polymerizing an appropriate polysaccharide with acrylonitrile or methacrylonitrile, with methyl or ethyl acrylate, with acrylic or methacrylic acid, or with acrylamide or methacrylamide, and thereafter hydrolyzing the resulting polymer in whole or in part with aqueous alkali. Alternatively, the polymer containing the carboxylate group may be prepared by polymerizing the alkali metal salt of acrylic or methacrylic acid. The procedures of carrying out graft-copolymerization of olefinically unsaturated chains onto cellulose and starch are well known in the art. Thus, grafting of the hydrophilic material onto a starch or cellulose backbone can be accomplished simultaneously with the formation of the hydrophilic polymeric material in an aqueous medium, because the peroxide catalyst used to copolymerize the various monomers forms a redox catalyst system in combination with a reducing agent and thus also serves to effect chain transfer onto the starch or cellulose backbone. Suitable reducing agents for this purpose are cerous ion, ferrous ion, cobaltous ion, $(NH_4)_2S_2O_8$, cuprous ion, and the like. The desired ions can be supplied in the form of salts such as cerous ammonium nitrate, ferrous ammonium sulfate, and the like. Graft copolymerization of olefinically-unsaturated chains can also be effected by irradiation (ultraviolet-, gamma-, or X-radiation) or by heating in an aqueous medium in the presence of an emulsifier.

Powdered starch or cellulose fibers or pulp can be slurried in water containing a graft copolymerization catalyst system and the monomer or monomers added to the slurry and polymerized in situ at ambient temperature or about depending on the catalyst employed. In this manner a portion of the formed hydrophilic polymer may also be physically entrapped into the polysaccharide backbone material during the polymerization process. The preparation of suitable starting materials for practicing the present invention is also illustrated in U.S. Pat. Nos. 2,922,768, 3,256,372, 3,661,815, 3,935,009, 4,028,290, 4,076,663 and 4,105,033. Suitable starch polyacrylates are available commercially such as SGP 5025 (General Mills or Henkel) and STASORB (A. E. Staley).

Suitable polysaccharides acrylates are those in which the hydrophilic chain loading on the backbone is within the range of about 10 percent by weight to about 90 percent by weight, preferably about 40 to about 80 percent by weight of the graft co-polymer. The polymers produced are dried at atmosphere pressure to drive off the water to produce a relatively stiff and brittle material which may be comminuted into powder of particle size of at least 1 micron. Preferably, the particles are no less than about 50 microns and no greater than about 1000 microns. Most preferably they are in the range of about 70 to about 325 microns.

A fourth type of absorbent suitable in the present invention is cross-linked carboxymethylcellulose (CMC). Suitable cross-linked carboxymethylcellulose are those which may be prepared by heat treatment or wet cross-linking of the sodium salt of carboxymethylcellulose having from about 0.5 to about 1 carboxymethyl group for each anhydroglucose unit. In wet cross-linking, reagents bifunctional with respect to cellulose such as epichlorohydrin may be employed.

A representative method for the preparation of absorbent of the class cross-linked carboxymethylcellulose is heating finely divided particulate form of water-soluble alkali metal salt of carboxymethylcellulose having from about 0.5 to about 1 carboxymethyl group for each anhydroglucose unit to a temperature between about 130° C. and about 210° C., generally from a few minutes to several hours to obtain products which retain their physical appearance when dry but when suspended in water show reduced solubility and a new capacity of absorbing water to form swollen gel particles as more fully described in U.S. Pat. No. 3,639,239. The particles, if not of desired size, may be comminuted to powder of particle size preferably in the range of about 50 microns to 1000 microns. Suitable cross-linked carboxymethylcellulose are available as AQUASORB from Hercules.

The matrix in the absorbent product of the present invention comprises a thermoplastic co-polyester polymer as hereinafter defined and exhibiting properties hereinafter described.

The co-polyester is essentially a polymer of at least two identifiable ester units which may be represented by the formulas and wherein X and X' are nuclei of dicarboxylic acids and Y and Y' are nuclei of aliphatic diols. The different ester units may arise from the condensation of (a) two different acids with the same diol, (b) two different diols with the same acid, or, (c) two different acids and two different diols. By "co-polyesters" is meant to include random and segmented co-polyesters as well as copolyesters with alternating units formed by copolymerization. By "random" is meant that the ester polymer units are not usually in a definite pattern. By "segmented" is meant there is a polymer block of a given ester unit joined to a polymer block of another ester unit through an ester linkage. Generally, one ester unit of the co-polyester is highly crystalline and one substantially less crystalline or even non-crystalline. It is not intended that the term "copolyester" embrace "homopolyesters" which are copolymer of a single dicarboxylic acid and a single diol since such polymers do not have properties suitable for the products contemplated in the present invention. Textile polyesters also are not suitable in the present invention.

Among the aromatic and aliphatic dicarboxylic acids suitable in co-polyesters are terephthalic acid, isophthalic acid, oxalic acid, maleic acid, succinic acid, glutaric acid, adipic acid, suberic aciq, azelaic acid, sebacic acid and the like.

Aliphatic diols used in the polyesters include ethylene glycol, 1,3-propylene glycol, diethylene glycol, dipropylene glycol, butylene glycol, tetramethylene glycol, trimethylene glycol and the like. Preferred aliphatic diols are straight chain alkylene diols having from 2 to 4 carbon atoms.

Representative co-polyesters may be mentioned the following: Poly(ethylene terephthalate-co-ethylene azelate), poly(ethylene terephthalate-co-butylene adipate), poly(ethylene terephthalate-co-1,2-propylene terephthalate), poly(butylene terephthalate-co-butylene isophthalate), poly(ethylene terephthalate-co-ethylene sebacate), poly(ethylene terephthalate-co-tetramethylene terephthalate), poly(ethylene terephthalate-co-ethylene adipate), poly(ethylene terephthalate-co-trimethylene terephthalate), and the like, including polyesters described on pages 77–80 of "Encyclopedia of Polymers, Science and Technology," Vol. XI, John Wiley & Sons (1977). Random co-polyesters frequently may be identified by the relative amounts of component diols and acids as in U.S. Pat. No. 3,699,189. Such polyesters are also within the scope of suitable matrix polymer.

The co-polyesters normally possess a thermal softening temperature below about 225° C. (437° F.). The preferred co-polyesters have an extrusion temperature within the range from about 325° to about 425° F. Suitable co-polyesters may be characterized by a torque property which can be measured by working in a recording torque dynamometer (Plasti-Corder ®EPL-V750 manufactured by C. W. Brabender Co., Hackensack, N.J.). When worked at 75 r.p.m. at 420° F. using a REE 6 mixing head, suitable co-polyesters will exhibit a torque value of less than about 1000 meter grams, preferably in the range of from about 200 to about 700 meter grams at this temperature. These values may be converted to poises by employing the following formula $$\frac{\text{torque} \times 388}{\text{r.p.m.}} = \text{poise}$$

Thus, when expressed in poises, the esters should show torque properties of less than about 5200 poises, preferably about 1000 to 3600 poises. Generally the co-polyesters having the foregoing suitable properties are in the number average molecular weight range of about 20,000 to 200,000, preferably about 30,000 to 75,000.

Co-polyesters may be made by conventional condensation polymerization procedures such as esterification of dicarboxylic acids or acid derivatives, e.g., esters or acid halides with diols, usually with temperatures in the range of from about 150° to 250° C., but sometimes as high as 280° C. with the formation of a co-polyester polymer. The reaction is usually carried out in the presence of excess diol to compensate for the loss of diol during codistillation with liberated water of reaction; it may be carried out in the presence of catalysts.

Another method for carrying out the reaction is ester interchange employing diols with dicarboxylic acid diesters or employing dicarboxylic acids with diol diesters. These and other methods may be found in the art including "Encyclopedia of Polymer Science and Technology," Vol. II, pages 88–113.

Segmented co-polyesters useful as matrix materials also may be prepared employing similar procedures applied in a step-wise manner. In one representative procedure, a low molecular weight alkyl diester of one or more dicarboxylic acid is heated with an appropriate long chain and excess short chain diol in the presence of catalyst at about 150° to 200° C. with the distillation of the low molecular weight alcohol formed in the interchange. Heating is continued until the alcohol evolution is complete to obtain a very low molecular weight prepolymer which can be converted to high molecular weight segmented co-polyester by heating the prepolymer with a long chain diol and distilling off excess short chain diol preferably at reduced pressures and elevated temperatures in the presence of antioxidants. Representative preparations may be found in U.S. Pat. No. 3,832,314 and 3,932,326. Suitable polymers are also available commercially under VPE designations from Goodyear Tire & Rubber Company, under KODAR ® designations from Eastman Chemical Company and DYVAX ® designations from E. I. Du Pont de Nemours & Co. Inc.

Embraced within the scope of polyesters are certain of the alloys of co-polyester as above defined and block polymer, such alloys being those having essentially plastic film forming properties as disclosed and claimed in copending application, Ser. No. 054,540, filed July 5, 1979, in the name of Ralf Korpman and incorporated by reference. In the alloy, the block copolymer consists essentially of an A-B-A or A-B block copolymer or a mixture thereof in which A represents an alkenylarene polymer block and B represents a polymer block of a conjugated lower aliphatic diene or a lower aliphatic alkene. In the alloy, the block copolymers are those in which the "A" block portion has a number average molecular weight in the range of from about 8000 to 30,000, and the "B" block portion has a number average molecular weight preferably in the range of from about 45,000 to about 180,000. The "A" blocks constitute from about 5 to about 50 percent by weight of the block copolymer. The number average molecular weight of the block copolymer is in the range of about 75,000 to 200,000 for linear copolymers and 125,000 to 400,000 for radial copolymers. The alloys intended for the matrixes in the present invention are only those in which the co-polyester component is the major component of from 55 to 95 percent by weight and the block copolymer component is the minor component of from 45 to 5 percent by weight.

The absorbent product of the present invention may be prepared by several methods none of which necessitate the use of an aqueous environment, thus eliminating the need for extended drying procedures. The preferred method may depend on the particular absorbent employed or whether it is desired to have the absorbent on one surface only.

When the absorbent is stable to the extrusion temperature of the matrix polymer and/or when the particulate absorbent is to be uniformly dispersed throughout the matrix, rather than on one surface, the product may be prepared by extrusion. Some of the absorbent which are extrudable include polyacrylate as previously defined, sulfonated polystyrene, poly(alkylene oxide), and the like.

In employing the extrusion method, the matrix polymer and the absorbent polymer are thoroughly blended together and extruded. Preblending is highly desirable if there is to be a high loading of the absorbent. If the level of absorbent to be dispersed is low, i.e., about 5 to 15 parts by weight per 100 parts by weight of matrix polymer, the components may be fed directly into the extruder without preblending. However, it is preferred that the absorbent polymer and the matrix polymer be preblended with heating to a uniform dispersion of the particulate absorbent in the molten matrix polymer, and the resulting uniform blend after cooling be pelletized, crushed, flaked or otherwise reduced to a size suitable for feeding into an extruder, or the molten blend is fed directly into the extruder and the extrusion carried out to obtain a nondisintegrative absorbent product comprising a water-insoluble substantially non-swelling matrix of a thermoplastic polymer having uniformly dispersed throughout, particulate, water-insoluble but water-swellable organic polymer absorbent in the form of a film, filament, tubing or other extrudable shaped. In this method, the absorbent is preferably in the form of a powder, i.e., particle size of $10^3$ microns in diameter or less. The preblending preferably is carried out in the temperature range of from about 225° to 275° F. The extrusion is preferably carried out in the temperature range of from about 300° F. to about 450° F. While not essential, it has been found that the addition of a minor amount, e.g., from about 5 to about 10 parts by weight per 100 parts by weight of matrix polymer, of an A-B-A block copolymer is desirable to facilitate extrusion. The extrusion method is particularly suitable for obtaining non-disintegrative absorbent product in the form of very thin films and monofilaments. The product will have absorbent dispersed throughout as seen in FIGS. 1, 3 and 5 of the drawings.

The extrudable compositions which are preferably formed by pre-blending and comprising thermoplastic matrix polymer and particulate polymer absorbent constitute an aspect of the present invention. The composition may include minor amounts of materials generally added to extrudable film forming compositions. Representative of such additives are antioxidants such as 2,5-ditertiary-amylhydroquinone, zinc salts of alkyl dithiocarbamates; fillers and pigments such as zinc oxide, titanium dioxide, calcium carbonate, and the like. In addition to the conventional additives, small amounts of wetting agents may be included which will facilitate initiation of aqueous fluid uptake by the absorbent. In addition, a thermoplastic-elastomeric block copolymer of the same type previously described for alloy compositions may be included in very small amounts up to about 10 percent without altering the properties of the plastic matrix polymer. Generally, the extrudable compositions comprise from about 5 to about 200 parts of polymer absorbent per 100 parts by weight of matrix polymer.

Preferred extrudable compositions are those which comprise a synthetic polyacrylate and a co-polyester matrix polymer. As previously indicated, the expression "acrylate" includes polymers which have any of acid ester, amide or salt acrylate groups or mixtures thereof. The compositions comprise from about 5 to about 500 parts of acrylate polymer per 100 parts of co-polyester, preferably from about 50 to 150 parts of acrylate polymer per 100 parts of co-polyester.

The extrudable composition also may be employed in a hot melt casting technique. Thus, instead of cooling the molten blend and pelletizing for extrusion, the molten composition may be cast to produce a free film or a coating on a substrate.

Absorbent products in which the particulate absorbent is to be supported by the matrix primarily on a surface may be prepared by a process in which the matrix is first formed and the absorbent incorporated thereon. This process is applicable in the preparation of absorbent product regardless of the chemical nature of absorbent polymer employed.

One modification of this general procedure contemplates incorporation of the absorbent polymer substantially at the time of formation of the matrix. In this method, the matrix polymer is extruded into whatever shape is contemplated, generally a film or a monofilament, and the absorbent is applied on the surface of the molten curtain or filament. The absorbent on contact becomes partially imbedded in the still molten surface and becomes permanently imbedded on cooling. The operation may be carried out by modification of the extrusion equipment in ways known in the art. For imbedding in a film, the particulate absorbent polymer may be spread or dusted on the film as it leaves the die. For incorporating on the surface of a filament, a similar procedure may be employed using a die adapter.

Another method employs a pre-formed matrix and the use of an adhesive composition in which there is a partial imbedding of the absorbent simultaneously with adhesion, and the effect is made permanent by the passing of the material through drying ovens. In one of these modifications, a solvent dispersed non-pressure sensitive adhesive composition is coated on the surface of an extruded film or filament and the absorbent applied on the surface of the solvent wetted film prior to passage through the ovens. In such method, any organic solvent coatable adhesive composition may be employed. In a second modification of this general method, a pressure-sensitive coating adhesive composition is applied to the surface of an extruded film or filament and the absorbent applied to the adhesive surface.

The absorbent product prepared by any one of the foregoing methods, particularly the products in the shape of films, may be further modified to form a discontinuous planar surface. Such surface may be reticulated or may contain embossed patterns of protrusions and depressions. Reticulated films are of special value for superior rate of fluid uptake. Preparation of absorbent products of films with discontinuous surfaces may be carried out employing procedures well known in the art for forming discontinuous surfaces but employing herein before described procedures for imbedding.

The following examples illustrate the invention but are not to be construed as limiting:

EXAMPLE I

An extrudable composition of 100 parts by weight of a co-polyester compound (obtained as VPE 5571 from Goodyear Tire & Rubber Co.) and believed to be poly-(ethylene terephthalate-co-ethylene azelate) and 40 parts of polyacrylate powder (Permasorb AG) were thoroughly blended at 350° F. and the resulting molten blend cooled, pelletized and the pellets fed into the hopper of an extruder simultaneously with a minor amount of commercially available styrene-isoprene (S-I) block copolymer (Solprene 311, Phillips Petroleum Company) and extruded at a temperature of about 350° F. to form a film 5 mils in thickness having the absorbent dispersed throughout. The film immediately swells when contacted with water at room temperature.

EXAMPLE II

In another operation, 75 parts by weight of VPE 5571, 25 parts by weight of Solprene-311 and 50 parts by weight of Permasorb AG were thoroughly blended, pelletized, and extruded in a similar manner to form a film 3 mils in thickness having the absorbent uniformly dispersed throughout. The film absorbs water rapidly.

EXAMPLE III

In a still further similar operation, 100 parts of a co-polyester compound (obtained as VPE 4709 from Goodyear Tire & Rubber Co.) and thought to be poly(ethylene terephthalate-co-1, 2-propylene terephthalate) co-polyester and 40 parts of polyacrylate absorbent (Sanwet, Sanyo Company) are blended together at about 350° F., the molten blend cooled, pelletized and extruded simultaneously with about 5 parts of styrene-isoprene-styrene (S-I-S) block copolymer (Kraton 1107) to produce a 2 mil film having the polyacrylate absorbent dispersed throughout. The film swells immediately when contacted with aqueous saline solution.

EXAMPLE IV

In another similar operation, 100 parts of VPE-5571 and 2 parts of Permasorb AG are blended together with heating, pelletized and extruded to produce a film bearing absorbent uniformly dispersed throughout and suitable for use in small absorbent bandages.

EXAMPLE V

Cotton fabric is solvent coated with the following pressure-sensitive adhesive formulation:

| COMPONENT | PARTS BY WEIGHT |
| --- | --- |
| Kraton 1107 | 50 |
| Solprene 311 | 50 |
| Tackifier resin (Wingtack 95) | 80 |
| Zinc dibutyl dithiocarbamate | 2 |
| 2,5-ditertiarybutylhydroquinone | 1 |

(Wingtack 95 is a predominantly polymerized piperylene and isoprene available from Goodyear Tire & Rubber Co.)

The adhesive composition is applied in amount sufficient to deposit the pressure-sensitive adhesive on the fabric at the rate of 3 ounces per square yard and the resulting coated film passed through drying ovens maintained at about 300° F. After the coated fabric is thoroughly dried, a cross-linked carboxymethoxylcellulose absorbent (Aquasorb, Hercules) is uniformly applied to the surface of the film to produce a non-disintegrative absorbent product having the absorbent uniformly distributed on one surface thereof. The absorbent product on contact with an aqueous system shows immediate absorption of aqueous fluid.

EXAMPLE VI

A 1 mil polyester (VPE 5571) film is coated with the following adhesive formulation:

| COMPONENT | PARTS BY WEIGHT |
| --- | --- |
| SIS rubber (Kraton 1107) | 100 |
| Resin (Amoco 18-290) | 75 |
| Zinc dibutyl dithiocarbamate | 2 |
| 2,5-ditertiary-butylhydroquinone | 1 |
| Solids in toluene | 50% |

(Amoco 18-290 is poly(α-methylstyrene) resin offered by Amoco Chemical Co.)

To the surface of the freshly coated film, particulate starch polyacrylate absorbent, (SGP 5025, General Mills or Henkel), is applied in a substantially monomolecular layer and the resulting film passed through drying ovens (maintained at about 250° F.) to remove the toluene solvent and to obtain an absorbent film product bearing absorbent on one major surface thereof. The resulting film shows immediate absorption when contacted with saline solution.

EXAMPLE VII

VPE 5571 is extruded at 350° F. with the aid of about 5 percent by weight of Kraton 1107 to a film and granular starch polyacrylate absorbent (Stasorb, A. E. Staley Company) is applied on the surface of the molten curtain. The curtain is allowed to cool to obtain a nondisintegrative absorbent product bearing absorbent on one major surface thereof. The product shows good absorptive properties.

EXAMPLE VIII

The composition employed in Example I is extruded to form a monofilament of about 1 mil in diameter. The monofilament on contact with water readily absorbs water to form a swollen rope.

The absorbent products of the present invention are useful in many ultimate articles where absorption of aqueous fluids is desired, such as diapers, bandages, pads, blankets, packaging materials, agricultural blankets and the like. The absorbent products are particularly adapted to be employed in the manufacture of certain articles.

Figures 7, 8:
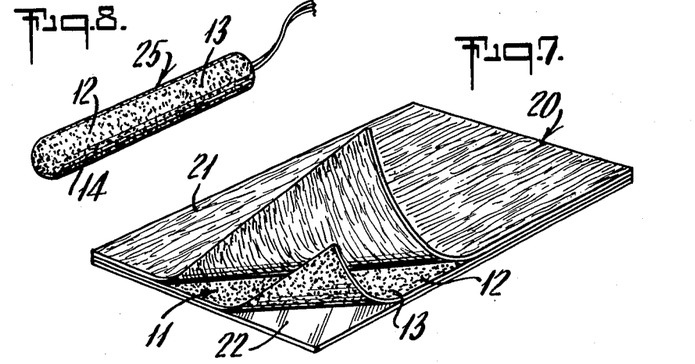
FIG. 7 is a perspective view of a diaper employing the absorbent product.
FIG. 8 is a view of a tampon made of the absorbent product.

The absorbent product in the configuration of a film may be employed as an absorbent layer in a thin diaper of little bulk but with high absorptive capacity. For such use, the absorbent film product may be either one having the absorbent dispersed throughout the film or one having the absorbent dispersed on one surface of the film. When the film product has absorbent dispersed throughout the film, it is desirable that the product be faced with a liquid permeable facing sheet 21 and be backed with a liquid impermeable backing sheet 22 to form a diaper 20 as seen in FIG. 7. The facing sheet may be of a conventional fluid permeable cellulosic material. The backing sheet may be of conventional fluid impermeable material such as polyethylene but it may be of co-polyester or of a thermoplastic-elastomeric film of the same composition as the backing film described in U.S. Pat. No. 4,024,312. A backing of thermoplastic elastomeric film is advantageous in exhibiting stretchability to accommodate the swelling which would occur in use. When the film product is one that has absorbent dispersed on one side of the film, the film product may serve the function of both the absorbent layer and the backing layer, the side of the film not bearing the absorbent performing the function of a backing. The absorbent film product in the latter embodiment generally would be of a heavier guage which can be determined by the skilled in the art.

A film product having absorbent dispersed throughout the matrix may also be employed as a coating on a substrate. In such application, an extrudable composition is extruded onto a substrate film in a conventional manner. It also may be extrusion coated onto an elongated substrate as seen in FIG. 6.

The absorbent product having absorbent dispersed throughout the matrix may be extruded through a die fitted with a cylindrical orifice to produce a rope or flexible rod. By the use of a cross-head die, a supporting element in the form of a string, monofilament or wire may be coated with a composition such as the one previously described to obtain a coated core substrate which may serve as the basis of a slender tampon 25 such as illustrated in FIG. 8. Such tampon may be of a conventional length but have a diameter in the range of about 50 mils to about 400 mils. The advantage of a tampon made of the absorbent product of the present invention is the slender quality of the article to provide for ease in insertion while still having the same or greater absorptive capacity as a tampon of much larger dimensions.

EXAMPLE IX

The film product of Example I is incorporated between a water permeable diaper facing and a water-impermeable diaper backing to produce an absorbent diaper having a thickness approximately 20 to 25 mils compared to a thickness of about 140 mils for a conventional diaper.

EXAMPLE X

The extrudable composition of Example I is extruded intermittently via a cross-head die onto a cotton string forming intermittently coated lengths, each coated length being about 1.7×10 and about 200 mils in diameter. On completion of the extrusion, the string is cut in the uncoated part to form slender tampons.

I claim:

1. A composition suitable for preparing an absorbent product by extrusion in the absence of water comprising:
   (a) a co-polyester of at least two different ester units, each ester unit being a condensation product of dicarboxylic acid and an aliphatic diol, said ester units being represented by the formulas:

and wherein X and X' are nuclei of dicarboxylic acids and Y and Y' are nuclei of aliphatic diols, and wherein said co-polyester is characterized by having a thermal softening temperature below about 225° C.; and
   (b) an absorbent synthetic acrylate polymer.

2. A flexible non-disintegrative absorbent product which is capable of absorbing and retaining water, comprising a water-insoluble substantially non-swelling matrix of a thermoplastic co-polyester polymer bearing uniformly dispersed particulate, water-insoluble, water-swellable organic polymer absorbent, wherein said co-polyester is a polymeric ester of at least two different ester units, each ester unit being a condensation product of a dicarboxylic acid and an aliphatic diol, said ester units being represented by the formulas:

and wherein X and X' are nuclei of dicarboxylic acids and Y and Y' are nuclei of aliphatic diols, and wherein the co-polyester polymer possesses a thermal softening temperature below about 225° C., said product having been manufactured using a hot melt and in the absence of water.

3. A product according to claim 1 in which the absorbent has a particle size of from about 1 micron to about 2×10 microns in diameter and comprises from about 5 to about 200 parts per 100 parts by weight of matrix polymer.

4. A product according to claim 1 in which the matrix is in the form of a film or sheet.

5. A product according to claim 1 in which the matrix is in the form of a monofilament or rope.

6. A product according to claim 1 in which the polymer absorbent is a synthetic acrylate polymer or a modified polysaccharide.

7. A thin absorbent article comprising an absorbent product of claim 1 faced with a liquid permeable sheet.

8. An article according to claim 7 in which the absorbent product in addition is backed with a liquid impermeable sheet.

9. A tampon comprising an absorbent product of claim 2, said product being in the form of an elongated cylinder.

* * * * *

UNITED STATES PATENT AND TRADEMARK OFFICE
CERTIFICATE OF CORRECTION

PATENT NO. : 4,449,977

DATED : May 22, 1984

INVENTOR(S) : Ralf Korpman

It is certified that error appears in the above—identified patent and that said Letters Patent is hereby corrected as shown below:

Claim 3, column 16, line 26 - "claim 1" should read -- claim 2 --.

Claim 4, column 16, line 31 - "claim 1" should read -- claim 2 --.

Claim 5, column 16, line 33 - "claim 1" should read -- claim 2 --.

Claim 6, column 16, line 35 - "claim 1" should read -- claim 2 --.

Claim 7, column 16, line 39 - "claim 1" should read -- claim 2 --.

Signed and Sealed this

Twenty-third Day of October 1984

[SEAL]

Attest:

Attesting Officer

GERALD J. MOSSINGHOFF

Commissioner of Patents and Trademarks